Figure 1:
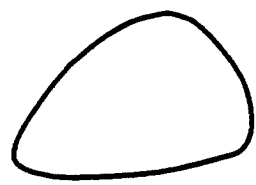
Figure 1:
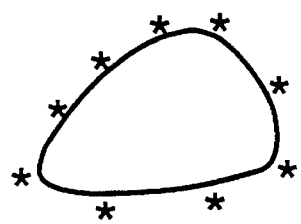
Figure 1:
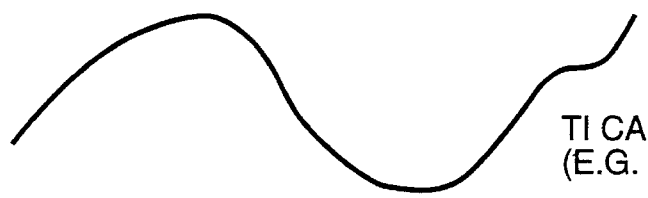
Figure 1:
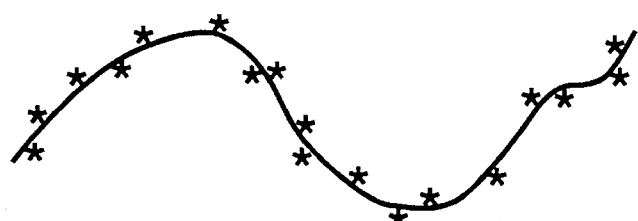

US005585100A

United States Patent [19]

Mond et al.

[11] Patent Number: 5,585,100
[45] Date of Patent: Dec. 17, 1996

[54] DUAL CARRIER IMMUNOGENIC CONSTRUCT

[75] Inventors: James J. Mond, Potomac; Andrew Lees, Baltimore, both of Md.

[73] Assignee: Henry Jackson Foundation, Rockville, Md.

[21] Appl. No.: 402,565

[22] Filed: Mar. 13, 1995

Related U.S. Application Data

[63] Continuation of Ser. No. 126,017, Sep. 24, 1993, abandoned, which is a continuation of Ser. No. 834,067, Feb. 11, 1992, abandoned.

[51] Int. Cl.⁶ .......................... A61K 39/385; A61K 39/02; A61K 39/12; A61K 39/116
[52] U.S. Cl. .......................... 424/193.1; 424/201.1; 424/202.1; 424/203.1; 424/280.1; 424/196.11; 424/197.11; 424/256.1; 424/244.1; 424/236.1; 424/240.1; 424/239.1; 530/403; 530/806
[58] Field of Search .......................... 424/193.1, 201.1, 424/202.1, 203.1, 280.1, 196.11, 197.11, 256.1, 244.1, 236.1, 240.1, 239.1; 530/403, 806

[56] References Cited

U.S. PATENT DOCUMENTS

| | | | |
|---|---|---|---|
| 4,169,137 | 9/1979 | Hirschfeld et al. | 436/547 |
| 4,356,170 | 10/1982 | Jennings et al. | 424/194.1 |
| 4,415,552 | 11/1983 | Dieiner et al. | 424/194.1 |
| 4,434,150 | 2/1984 | Azad et al. | 530/400 |
| 4,619,828 | 10/1986 | Gordon | 424/194.1 |
| 4,644,059 | 2/1987 | Gordon | 536/117 |
| 4,703,039 | 10/1987 | Hawiger et al. | 514/21 |
| 4,713,240 | 12/1987 | Wilkins et al. | 424/239.1 |
| 4,748,111 | 5/1988 | Dattagupta et al. | 435/6 |
| 4,769,237 | 9/1988 | Bittle et al. | 424/186.1 |
| 4,780,312 | 10/1988 | Talwar | 424/195.11 |
| 4,824,775 | 4/1989 | Dattagupta et al. | 435/4 |
| 4,830,852 | 5/1989 | Marburg et al. | 424/165.1 |
| 4,863,729 | 9/1989 | Zuckerkandl | 424/178.1 |
| 4,894,229 | 1/1990 | Polson et al. | 424/130.1 |
| 5,085,862 | 2/1992 | Klein et al. | 424/197.11 |
| 5,126,131 | 6/1992 | Dintzis et al. | 424/193.1 |
| 5,153,312 | 10/1992 | Porro | 530/405 |

FOREIGN PATENT DOCUMENTS

| | | |
|---|---|---|
| WO92/11029 | 7/1992 | European Pat. Off. . |
| 8808429 | 11/1988 | WIPO . |
| WO90/11778 | 10/1990 | WIPO . |

OTHER PUBLICATIONS

Baltz et al (1977) Eur. J. Immurol 7:218–222.
Hosokawa (1979) Immurology 38:291–299.
Tadakuma et al. (1982) J. Immurol. 128:206–210.
Watanabe et al (1983) Abstract Only Cell Immunol 79:345–357.
Yaffe et al (1983) J Immunol 130:632–635.
Geerligs et al (1988) J. Immunol Meth 106:239–244.
Dintzis et al (1989) J Immunol 143:1239–1244.
Boslego et al "Gonorrhea Vaccines" in *Vaccines & Immunotherapy* Cryz S. J ed. Pergamon Press, New York, 1991 pp. 211–223.
Kallings et al, Lancet I: 955–960, 1988.
Butcher G. A, Parisitology 98:315–327, 1989.
Patarroyo et al, Nature 328:629–632, 1987.

(List continued on next page.)

*Primary Examiner*—James C. Housel
*Assistant Examiner*—Julie Krsek-Staples
*Attorney, Agent, or Firm*—Finnegan, Henderson, Farabow, Garrett and Dunner, L.L.P.

[57] ABSTRACT

A dual carrier immunogenic construct comprised of at least one primary carrier comprising large molecular weight molecule of greater than a 70 KD molecular weight and at least one secondary carrier comprising a T-dependent antigen conjugated to a primary carrier. The dual carrier immunogenic construct may further comprise moieties such as haptens and antigens. Such immunogenic constructs are suitable for use in the diagnosis, treatment, and prevention of diseases.

31 Claims, 14 Drawing Sheets

OTHER PUBLICATIONS

Inman J. K., J Immunol. 114(2): 704–709, 1975.

Stites et al, eds *Basic & Clinical Immunology,* Appleton & Lang Norwalk, CT 6th Ed. p. 703 1987.

*Stedman's Medical Dictionary,* Williams & Wilkins, Baltimore 24th Ed., 1982, p. 1526.

Mitani et al., Infection and Immunity, "Immunoglobulin E–Suppressing and Immunoglobulin G–Enhancing Tetanus Toxoid Prepared by Conjugation with Pullulan," vol. 36, No. 3, pp. 971–976 (Jun. 1982).

Beuvery et al., "Vaccine potential of meningococcal group C polysaccharide–tetanus toxoid conjugate," J. Infect. 6:247–255 (1983).

Ahmad et al., The Journal of Immunology, 136:1223–1226, Restoration of In Vitro Responsiveness of XID B Cells to TNP–Ficoll by 8–Mercaptoguanosine (Feb. 1986).

Dancey et al., The Journal of Immunology, 122:638–642, Immunogenicity of Liposomal Model Membranes Sensitized with Dinitrophenylated Phosphati–dylethanolamine Derivatives Containing Different Length Spacers (Feb. 1979).

Anderson et al., The Journal of Immunology, 142:2464–2468, Effect of Oligo–saccharide Chain Length, Exposed Terminal Group, and Hapten Loading on the Antibody Response of Human Adults and Infants to Vaccines . . . (Apr. 1989).

Dick et al., Cruse J. M., Lewis R. E. (eds), Contributions to Microbiology and Immunology, Conjugate Vaccines, 10:48–114, Glycoconjugates of Bacterial Carbohydrate Antigens (1989).

Mosier et al., The Journal of Experimental Medicine, 139:1354–1360, Cellular Requirements for the Primary In Vitro Antibody Response to DNP–Ficoll, (1974).

Mosier et al., The Journal of Immunology, 119:1874–1878, The Ontogeny of Thymic Independent Antibody Responses In Vitro in Normal Mice and Mice With an X–Linked B Cell Defect (Dec. 1977).

Mond, J. J., Immunological Reviews, 64:99–115, Use of the T Lymphocyte Regulated Type 2 Antigens for the Analysis of Responsiveness of Lyb5 and Lyb5 B Lymphocytes to T Lymphocyte Derived Factors (1982).

Mond et al., The Journal of Immunology, 123:239–245, Analysis of B Cell Activation Requirements with TNP–Conjugated Polyacrylamide Beads (Jul. 1979).

Dintzis et al., The Journal of Immunology, 143:1239–1244, The Immunogeni–city of Soluble Haptenated Polymers is Determined by Molecular Mass and Hapten Valence (Aug. 1989).

Brunswick et al., The Journal of Immunology, 140:3364–3372, Picogram Quantities of Anti–Ig Antibodies Coupled to Dextran Induce B Cell Prolifer–ation (May 1988).

I. T CELL DEPENDENT (TD)

TD CARRIER
(E.G., TETANUS TOXOID)

IMMUNOGENICITY

+
−

HAPTENATED TD CARRIER
(E.G., TNP-TETANUS TOXOID)

+
−

II. T CELL INDEPENDENT (TI)

TI CARRIER
(E.G. DEXTRAN)

IMMUNOGENICITY

+ +

HAPTENATED T CARRIER
(E.G., TNP-DEXTRAN)

+ +

| ANTIGEN | SPECIFIC TITER |
|---|---|
| 1. OVALBUMIN-DEX | 364 |
| 2. β-LACTOGLOBULIN B -DEX | 337 |
| 3. LYSOZYME-DEX | 1666 |
| 4. APROTININ-DEX | 261 |
| 5. VACCINIA-DEX | 12,800 |
| 6. CHOLERA TOXIN | 794 |
| 7. CHOLERA TOXIN -DEX | 12,433 |
| 8. TETANUS TOXOID -DEX | 1,761 |
| 9. ALL OF ABOVE UNCONJUGATED Ag (EXCEPT CHOLERA TOXIN) | < 10 |

*FIG. 4*

PRP-TETANUS TOXOID

MALARIAL DERIVED PEPTIDE-MENINGOCOCCAL OUTER MEMBRANE PROTEIN

VIRAL PROTEIN, E.G., RSV F PROTEIN

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

Cys Asn Ile Gly Lys Val Pro Asn Val Gln Asp Gln Asn Lys
   1              5                           10

DUAL CARRIER IMMUNOGENIC CONSTRUCT

I. GOVERNMENT INTEREST

The invention described herein may be manufactured, licensed and used for governmental purposes without the payment of any royalties to us thereon.

This application is a continuation of application Ser. No. 08/126,017, filed Sep. 24, 1993, now abandoned; which is a continuation of application Ser. No. 07/834,067, filed Feb. 11, 1992, now abandoned.

II. FIELD OF THE INVENTION

This invention relates to a dual carrier immunogenic construct that enhances the effectiveness of active immunization for animals and humans and for development of antibodies to be used for passive immunoprophylaxis or therapy and as scientific or diagnostic reagents.

III. BACKGROUND OF THE INVENTION

In the process of vaccination, medical science uses the body's innate ability to protect itself against invading agents by immunizing the body with antigens that will not cause the disease but will stimulate the formation of antibodies that will protect against the disease. For example, dead organisms are injected to protect against bacterial diseases such as typhoid fever and whooping cough, toxins are injected to protect against tetanus and botulism, and attenuated organisms are injected to protect against viral diseases such as poliomyelitis and measles.

It is not always possible, however, to stimulate antibody formation merely by injecting the foreign agent. The vaccine preparation must be immunogenic, that is, it must be able to induce an immune response. Certain agents such as tetanus toxoid are innately immunogenic, and may be administered in vaccines without modification. Other important agents are not immunogenic, however, and must be converted into immunogenic molecules before they can induce an immune response.

The immune response is a complex series of reactions that can generally be described as follows:

1. the antigen enters the body and encounters antigen-presenting cells which process the antigen and retain fragments of the antigen on their surfaces;
2. the antigen fragment retained on the antigen presenting cells are recognized by T cells that provide help to B cells; and
3. the B cells are stimulated to proliferate and divide into antibody forming cells that secrete antibody against the antigen.

Most antigens only elicit antibodies with assistance from the T cells and, hence, are known as T-dependent (TD). These antigens, such as proteins, can be processed by antigen presenting cells and thus activate T cells in the process described above. Examples of such T-dependent antigens are tetanus and diphtheria toxoids.

Some antigens, such as polysaccharides, cannot be properly processed by antigen presenting cells and are not recognized by T cells. These antigens do not require T cell assistance to elicit antibody formation but can activate B cells directly and, hence, are known as T-independent antigens (TI). Such T-independent antigens include *H. influenzae* type b polyribosyl-ribitol-phosphate and pneumococcal capsular polysaccharides.

T-dependent antigens vary from T-independent antigens in a number of ways. Most notably, the antigens vary in their need for an adjuvant, a compound that will nonspecifically enhance the immune response. The vast majority of soluble T-dependent antigens elicit only low level antibody responses unless they are administered with an adjuvant. It is for this reason that the standard DPT vaccine (diphtheria, pertussis, tetanus) is administered with the adjuvant alum. Insolubilization of TD antigens into an aggregated form can also enhance their immunogenicity, even in the absence of adjuvants. (Golub ES and WO Weigle, J. Immunol. 102:389, 1969) In contrast, T-independent antigens can stimulate antibody responses when administered in the absence of an adjuvant, but the response is generally of lower magnitude and shorter duration.

Four other differences between T-independent and T-dependent antigens are:

a) T-dependent antigens can prime an immune response so that a memory response can be elicited upon secondary challenge with the same antigen. Memory or secondary responses are stimulated very rapidly and attain significantly higher titers of antibody than are seen in primary responses. T-independent antigens are unable to prime the immune system for secondary responsiveness.

b) The affinity of the antibody for antigen increases with time after immunization with T-dependent but not T-independent antigens.

c) T-dependent antigens stimulate an immature or neonatal immune system more effectively than T-independent antigens.

d) T-dependent antigens usually stimulate IgM, IgG1, IgG2a, and IgE antibodies, while T-independent antigens stimulate IgM, IgG1, IgG2b, and IgG3 antibodies.

These characteristics of T-dependent vs. T-independent antigens provide both distinct advantages and disadvantages in their use as effective vaccines. T-dependent antigens can stimulate primary and secondary responses which are long-lived in both adult and in neonatal immune systems, but must frequently be administered with adjuvants. Thus, vaccines have been prepared using only an antigen, such as diphtheria or tetanus toxoid, but such vaccines may require the use of adjuvants, such as alum for stimulating optimal responses. Adjuvants are often associated with toxicity and have been shown to nonspecifically stimulate the immune system, thus inducing antibodies of specificities that may be undesirable.

Another disadvantage associated with T-dependent antigens is that very small proteins, such as peptides, are rarely immunogenic, even when administered with adjuvants. This is especially unfortunate because many synthetic peptides are available today that have been carefully synthesized to represent the primary antigenic determinants of various pathogens, and would otherwise make very specific and highly effective vaccines.

In contrast, T-independent antigens, such as polysaccharides, are able to stimulate immune responses in the absence of adjuvants. Unfortunately, however, such T-independent antigens cannot stimulate high level or prolonged antibody responses. An even greater disadvantage is their inability to stimulate an immature or B cell defective immune system (Mond J. J., Immunological Reviews 64:99, 1982) (Mosier D. E., et al., J. Immunol. 119:1874, 1977). Thus, the immune response to both T-independent and T-dependent antigens is not satisfactory for many applications.

With respect to T-independent antigens, it is critical to provide protective immunity against such antigens to children, especially against polysaccharides such as *H. influenzae* and *S. pneumoniae*. With respect to T-dependent antigens, it is critical to develop vaccines based on synthetic peptides that represent the primary antigenic determinants of various pathogens.

One approach to enhance the immune response to T-independent antigens involves conjugating polysaccharides such *H. influenzae* PRP (Cruse J. M., Lewis R. E. Jr. ed., Conjugate vaccines in Contributions to Microbiology and Immunology, vol. 10, 1989) or oligosaccharide antigens (Anderson P. W., et al., J. Immunol. 142:2464, 1989) to a single T-dependent antigen such as tetanus or diphtheria toxoid. Recruitment of T cell help in this way has been shown to provide enhanced immunity to many infants that have been immunized. Unfortunately, only low level antibody titers are elicited, and only some infants respond to initial immunizations. Thus, several immunizations are required and protective immunity is often delayed for months. Moreover, multiple visits to receive immunizations may also be difficult for families that live distant from medical facilities (especially in underdeveloped countries). Finally, babies less than 2 months of age may mount little or no antibody response even after repeated immunization.

The current solution for protein or peptide T-dependent antigens is similarly disadvantageous. T-dependent antigens are often incorporated into adjuvants or other delivery systems. Such an approach, however, may be toxic or may induce non-specific enhancement of the antibody response (Dancey G. F., et al., J. Immunol. 122:638, 1979).

Moreover, these approaches with both T-dependent and T-independent antigens incorporate only a single T-dependent carrier to potentiate the immune response. Such approaches do not maximize recruitment of T-cell help. Moreover, these methods are extraordinarily limited and confined by the inability to administer multiple antigens on one carrier, and thus require numerous injections.

In another approach, investigators have conjugated a hapten such as Trinitrophenyl (TNP) to a T-independent carrier such as Ficoll® (an inert synthetic non-ionized high molecular weight polymer) of molecular weight 400K. Such a conjugate has been found to stimulate a T-independent response in mice in the absence of adjuvant (Mosier D. E., et al., J. Exp. Med. 139:1354 (1974)). This conjugate alone, however, could not stimulate immune responses in neonatal mice or in B cell immune defective mice (Mosier D. E., et al., J. Immunol. 119:1874, 1977). Responses of immune defective mice to this conjugate could only be induced in the presence of a particular adjuvant (Ahmad A. and Mond J. J., J. Immunol. 136:1223, 1986). This is disadvantageous for the reasons discussed previously.

In a further study, TNP was conjugated onto insoluble particles and found to be an effective in vitro immunogen for neonatal mice and immune defective mice, but only at very high density of hapten per bead (Mond J. J., et al., J. Immunol. 123:239, 1979). Another laboratory, Dintzis et al., demonstrated that the ratio of hapten to carrier, as well as the molecular mass of the carrier, strongly influences immunogenicity of a T independent conjugate and the antibody responses it stimulates (Dintzis R. Z., et al., J. Immunol. 143:1239, 1989).

Another attempted conjugate involved an anti-immunoglobulin antibody (anti-Ig) conjugated to a dextran (a glucose polymer) of high molecular weight ($2 \times 10^6$ daltons) to form an "anti-Ig Dex" conjugate. The conjugate was found to activate neonatal and mature B cells as well as B cells from immune defective mice at very low concentrations (Brunswick M., et al., J. Immunol. 140:3364, 1988). However, since anti-Ig Dex stimulates little or no T cell derived help and since it activates all B cells without regard to specificity, it could not provide an effective vehicle for a vaccine.

None of these approaches solved the problem because the constructs optimized only one type of immune response. For example, low molecular weight haptens conjugated onto T-independent carriers will optimize only the T-independent component of the anti-hapten response, and poorly immunogenic T-independent molecules conjugated onto T dependent carriers will have to rely on stimulation of T-dependent immunity and in soluble form this complex may be very limiting in activating T cells. Thus, there remains a need in the art for constructs that optimize both components. Such a construct would optimize both the T-independent component to specifically stimulate high levels of activation in antigen specific B cells as well as optimize the T-dependent component to simultaneously recruit T cell help. In addition, such a dual construct would rapidly induce high levels of antibody to both T dependent and T independent antigens in neonates, adults and immunodeficient animals and humans.

There is also a need in the art for a construct to which multiple antigens could be attached so that a number of antigens could be presented in one injection. A vaccine that could immunize an individual with multiple antigens on a single construct would be extremely valuable.

In sum, there is a need in the art (a) for a construct that optimizes both T-independent and T-dependent antigen components to stimulate a very rapid and large antibody response that will persist over long periods of time in both children and adults, as well as in individuals that have immunodeficiencies (b) for a construct to which multiple antigens or other immune enhancing adjuvants could be attached; and (c) for a construct that would rapidly stimulate antibodies, either monoclonal or polyclonal, which could be employed for passive immunoprophylaxis or therapy, and for diagnostic, or research purposes.

IV. SUMMARY OF THE INVENTION

The present invention overcomes the problems and disadvantages of the prior constructs by providing a dual carrier immunogenic construct that improves immunogenicity. The dual carrier immunogenic construct comprises at least one primary carrier that is a large molecular weight molecule conjugated to at least one secondary carrier that is a T-dependent antigen. Such a primary carrier enables presentation of multiple copies of the secondary carrier at a relatively high antigenic density to both T and B cells. In addition, such a large backbone matrix acts as an efficient carrier for many secondary carriers so that a single construct could contain multiple antigenic specificities. In a preferred embodiment, the primary carrier is a large molecular weight T-independent antigen that can itself directly and potently activate B cells and that can serve as a large but relatively nondegradable backbone to carry many secondary carriers.

The secondary carrier is a T-dependent antigen. As a T-dependent antigen, the secondary carrier activates and recruits T cells to augment antibody production to itself as well as to other determinants which may be conjugated to itself or to the primary carrier. Multiple copies of secondary carriers may be conjugated to the primary carrier to significantly enhance T-cell activation and thereby augment antibody production against the secondary carrier.

In a preferred embodiment, the present invention also includes at least one moiety, such as a hapten and antigen, conjugated to a primary carrier or a secondary carrier. Conjugation permits the moiety to benefit from the T-cell help generated by the secondary carrier.

The dual carrier immunogenic construct of the invention also permits the conversion of non-immunogenic or poorly immunogenic molecules into strongly immunogenic molecules by conjugating the molecules onto the dual carrier construct. In addition, it is possible to conjugate immune enhancing adjuvants onto any of the carriers to further enhance immunogenicity. Preferably, such a dual carrier immunogenic construct is prepared from non-toxic components. In addition, such dual carrier immunogenic construct may reduce alterations of the antigenic sites, since protein conjugation to the primary carrier, such as dextran, involves minimal alteration to the carrier.

Finally, the dual carrier immunogenic construct of the invention can be applied to therapy, prophylaxis, diagnosis, and research.

Additional advantages and aspects of the invention will be set forth in the detailed description which follows, derived from that detailed description, or learned by practice of the invention.

To achieve the advantages and in accordance with the purpose of the invention, as embodied and broadly described in this specification, the invention comprises a dual carrier immunogenic construct made up of at least one primary carrier that is a large molecular weight molecule of greater than 70 KD molecular weight conjugated to at least one secondary carrier that is a T-dependent antigen. The immunogenicity of the construct is greater than at least one carrier alone. In a preferred embodiment, the primary carrier is a T-independent antigen and the secondary carrier is a protein. In another preferred embodiment, at least one moiety is conjugated to at least one carrier of the construct. The immunogenicity of the conjugated moiety is greater than the unconjugated moieties.

Another aspect of the invention relates to a vaccine comprising at least one of the dual carrier immunogenic constructs and a pharmaceutically acceptable carrier. A still further aspect of the invention relates to a method of treating a patient by administering an immunostimulatory amount of the vaccine.

Another aspect of the invention relates to a method of preparing antibodies by immunizing a host with the vaccine so that antibodies directed against immunogens are produced and then isolating the antibodies or B cells that can be used to produce monoclonal antibodies. In a further aspect, the invention relates to an immunotherapeutic composition comprising such antibodies. In a still further aspect, the invention relates to a method of treating patients by administering a therapeutically effective amount of the immunotherapeutic composition. In another aspect, the invention relates to a diagnostic or research reagent comprising such antibodies.

The accompanying drawings, which are incorporated in and constitute a part of this specification, illustrate several exemplary embodiments of the invention and, together with the description, serve to explain the principles of the invention.

The above and various other objects, features and many of the attendant advantages of the invention will be better understood upon a reading of the following detailed description when considered in connection with the accompanying drawings.

V. BRIEF DESCRIPTION OF THE DRAWINGS

FIG. 1 Illustrative depiction of the two classical types of antigens based on their T cell requirements. T-independent antigens (and haptenated TI antigens) stimulate responses in the absence of T cells, and T-dependent antigens (and haptenated TD antigens) require T cell participation for elicitation of optimal antibody responses.

Figure 2:
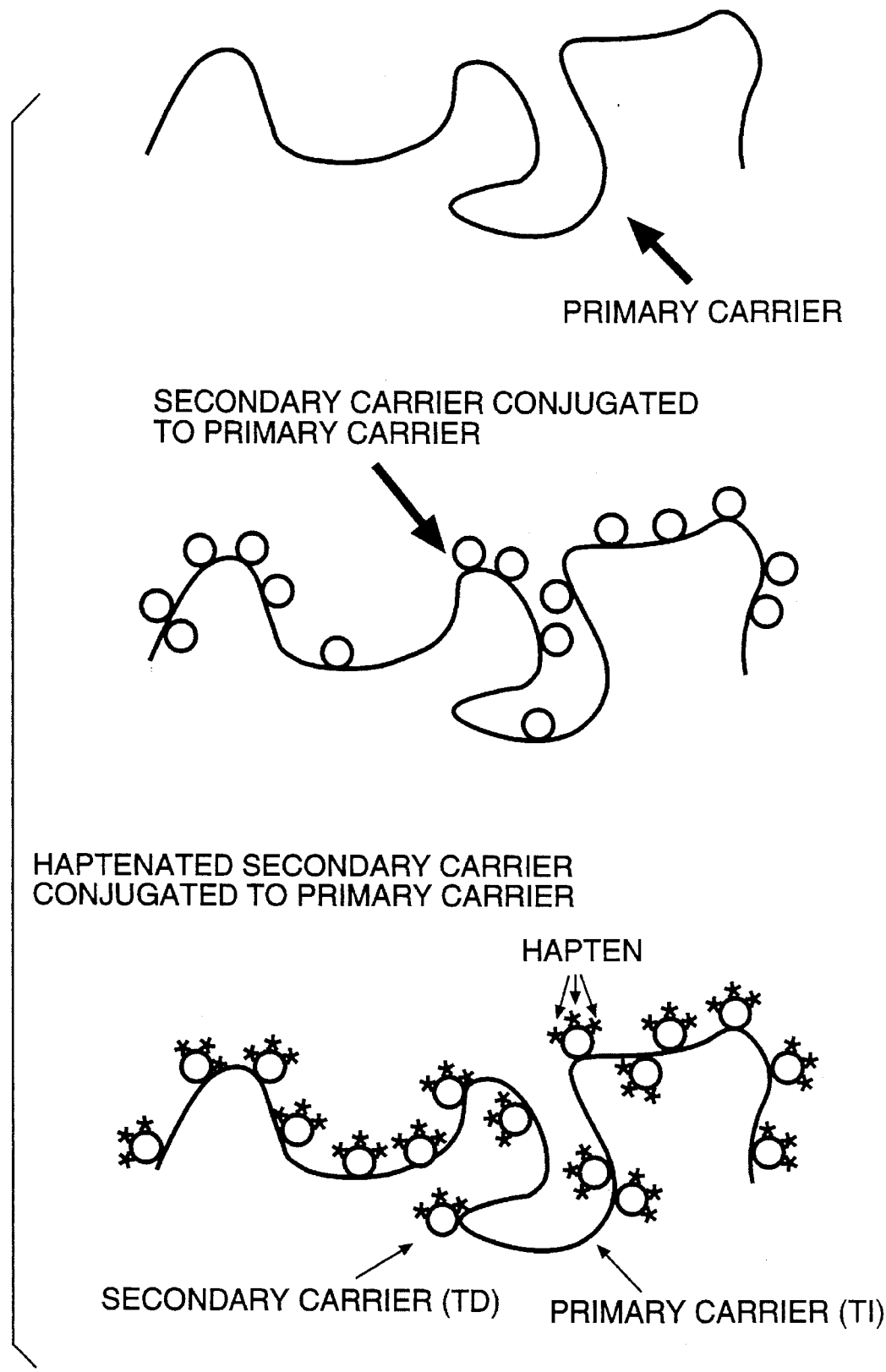

FIG. 2 Schematic drawing of one embodiment of dual carrier immunogenic construct:

the primary carrier is a high molecular weight polymer (HMWP), for example Dextran (Dex);

the secondary carrier, conjugated to Dex, can be any substance that stimulates high levels of T cell activation;

the hapten is any low molecular weight molecule, such as an oligosaccharide, polysaccharide, peptide, drug, etc., which is conjugated to the secondary carrier.

Figure 3:
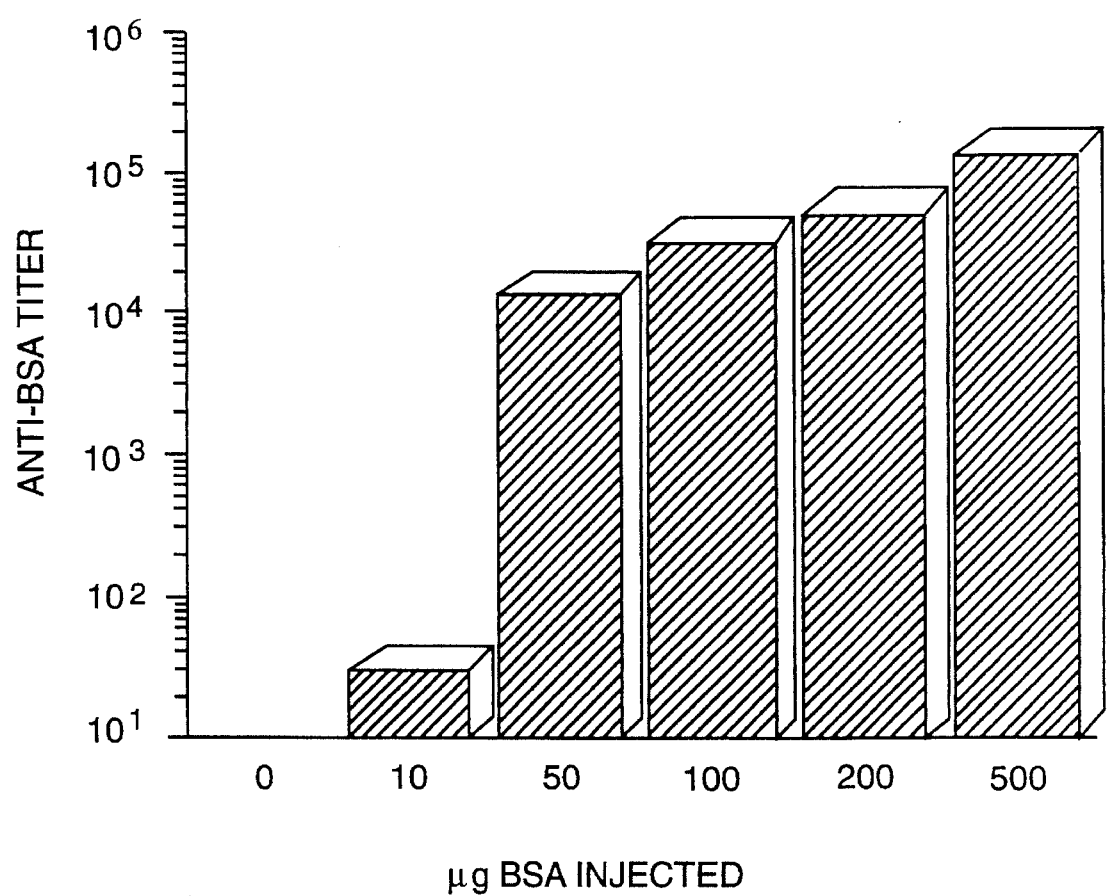

FIG. 3 Graphic representation of the dose response to BSA-Dex conjugate. Serum IgG1 antibody titers to bovine serum albumin (BSA) were measured in mice immunized intravenously with BSA-Dex in PBS conjugates at doses ranging from 10–500 µg/mouse. Mice were bled 14 days after immunization and antibody titers determined by ELISA. Unconjugated BSA is not immunogenic in mice. This figure shows that conjugation to Dex converts BSA into a highly potent immunogen.

FIG. 4 Chart depicting proteins of various sizes that were conjugated to Dex and injected intravenously (IV) into mice at the indicated doses. Serum IgG1 antibody titers were determined by ELISA. In contrast to the conjugated proteins, immunization of mice with antigens not coupled to dextran gave no detectable antibody formation (titers were less than 10) except for the cholera toxin immunization which gave detectable titers, albeit significantly less than the Dex conjugate. This figure shows that conjugation of different proteins to Dex converts them into effective immunogens.

Figure 5:
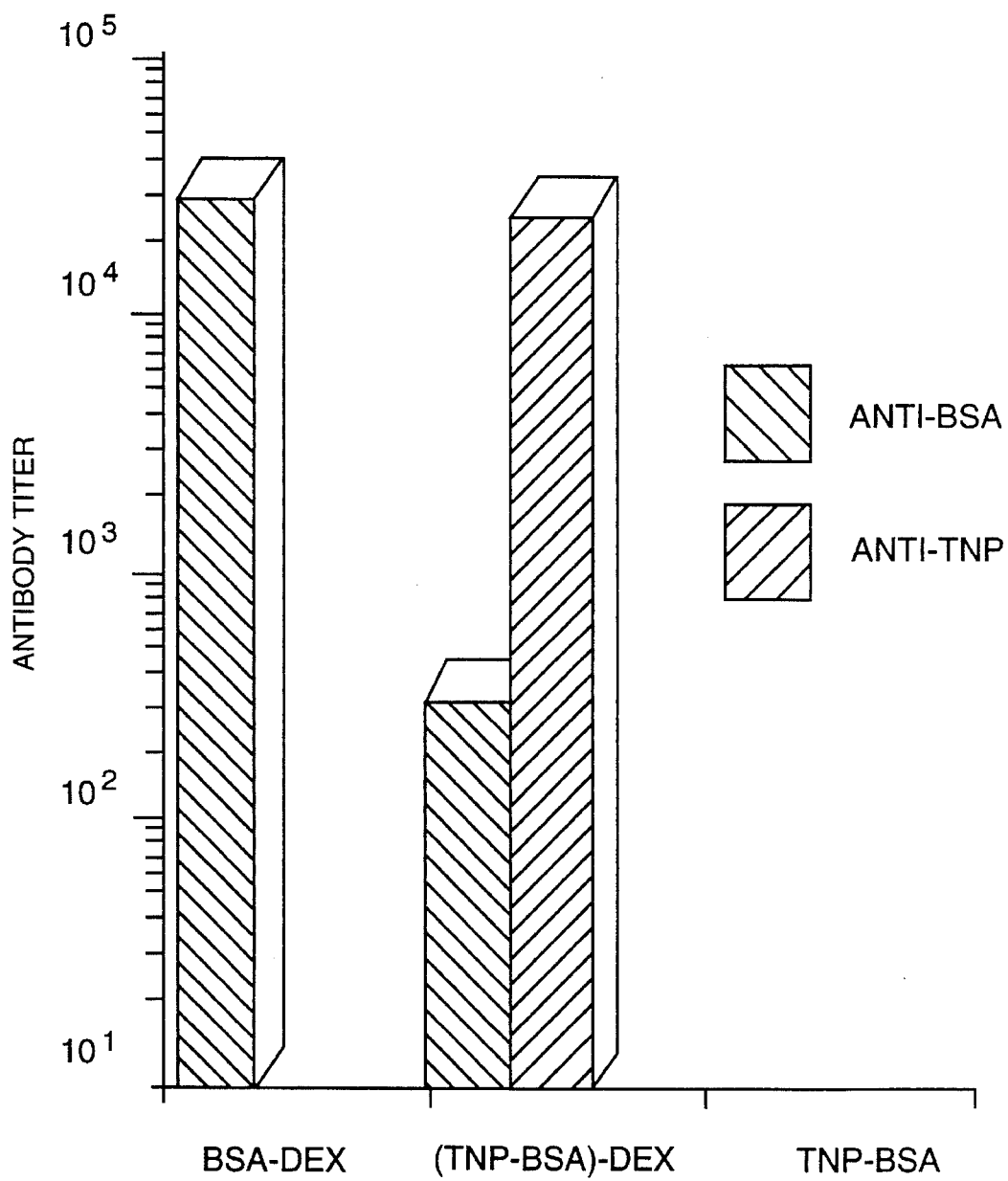

FIG. 5 Graphic representation of the response to haptenated BSA. Mice were immunized with trinitrophenylated BSA (TNP-BSA) (50 µg) or with TNP-BSA conjugated to Dex (TNP-BSA Dex) (50 µg) and were bled 21 days later. Anti-TNP titers were measured by ELISA. This figure demonstrates that a good antibody response to both BSA and TNP is elicited by using Dex as the primary carrier and BSA as the secondary carrier. Thus, the conjugation of TNP to the secondary protein carrier molecule coupled with the conjugation of this complex to the primary carrier converted TNP into an effective immunogen.

Figure 6:
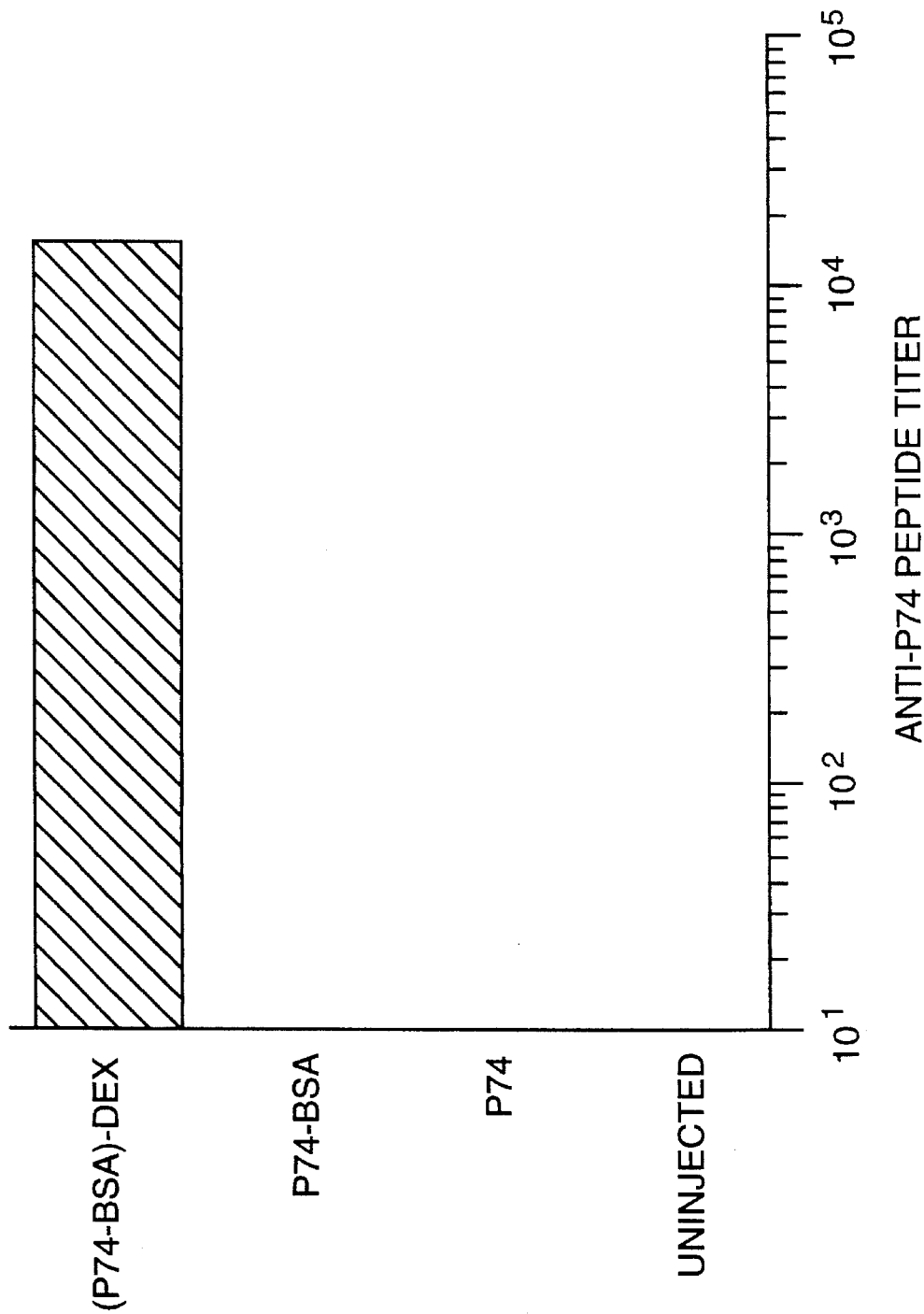

FIG. 6 Graphic representation of the anti-peptide response. This study supports the previous study shown in FIG. 5. It shows that the conjugation of the malarial derived peptide P74 (SEQ ID NO:1) to the secondary carrier, BSA, and the conjugation of this complex to the Dex primary carrier, converts a non-immunogenic peptide (P74, SEQ ID NO:1) into an effective immunogen. This is particularly relevant in demonstrating the utility of this construct for synthetic peptides.

Figure 7:
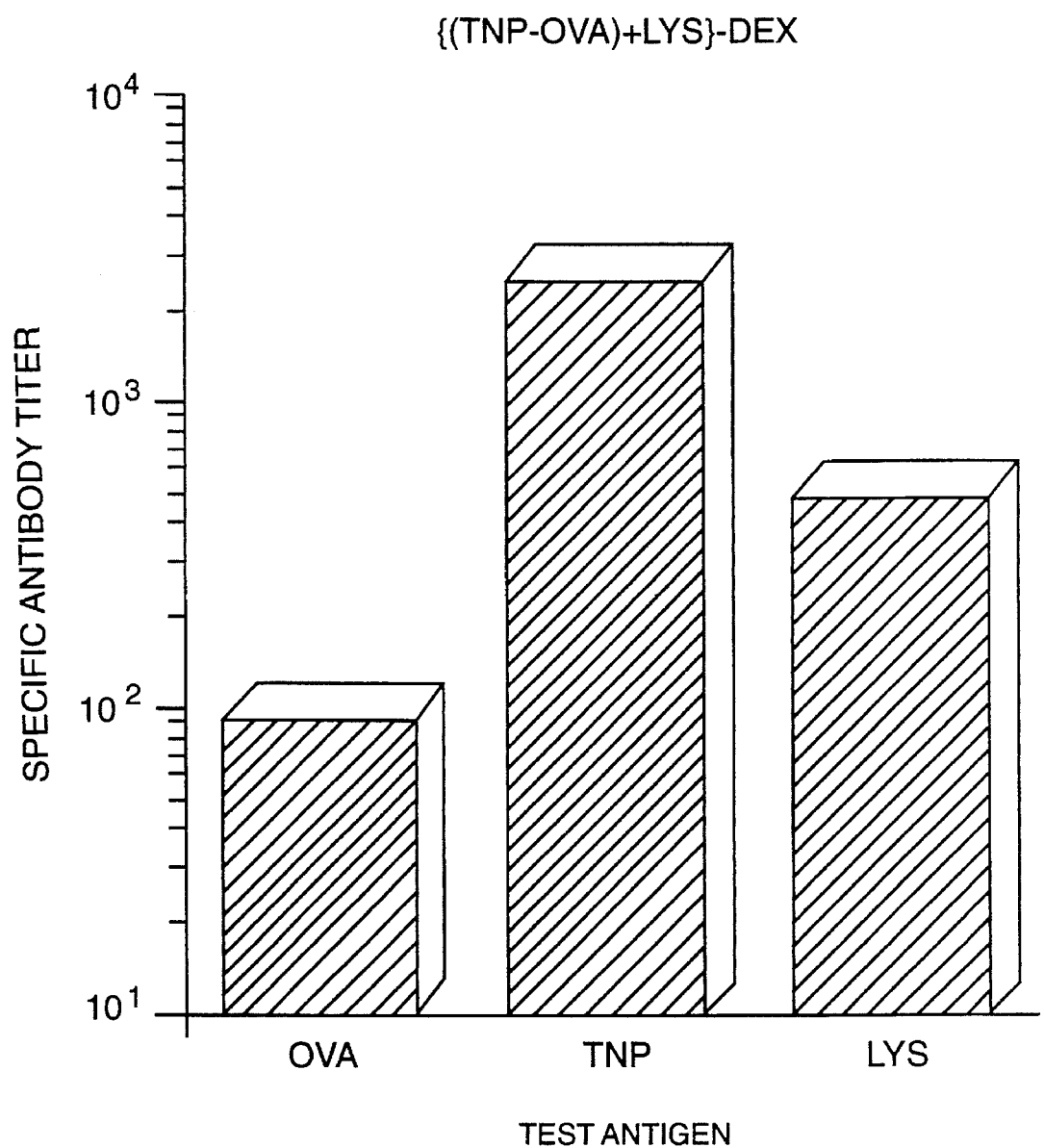

FIG. 7 Graphic representation of multiple antigens conjugated to dextran. This study evaluates the antibody response to a Dex complex which has been prepared by conjugating three antigenically different molecules to Dex. In this study, TNP coupled with ovalbumin (OVA), plus lysozyme (LYS) were conjugated to Dex and 50 µg of this conjugate was injected IV into mice. Nine days later mice were bled and sera titered by ELISA for anti-OVA, anti-TNP and anti-LYS antibody titers. This study demonstrates that a vaccine preparation can be made by conjugating multiple unrelated antigens onto the primary Dex carrier.

Figure 8:
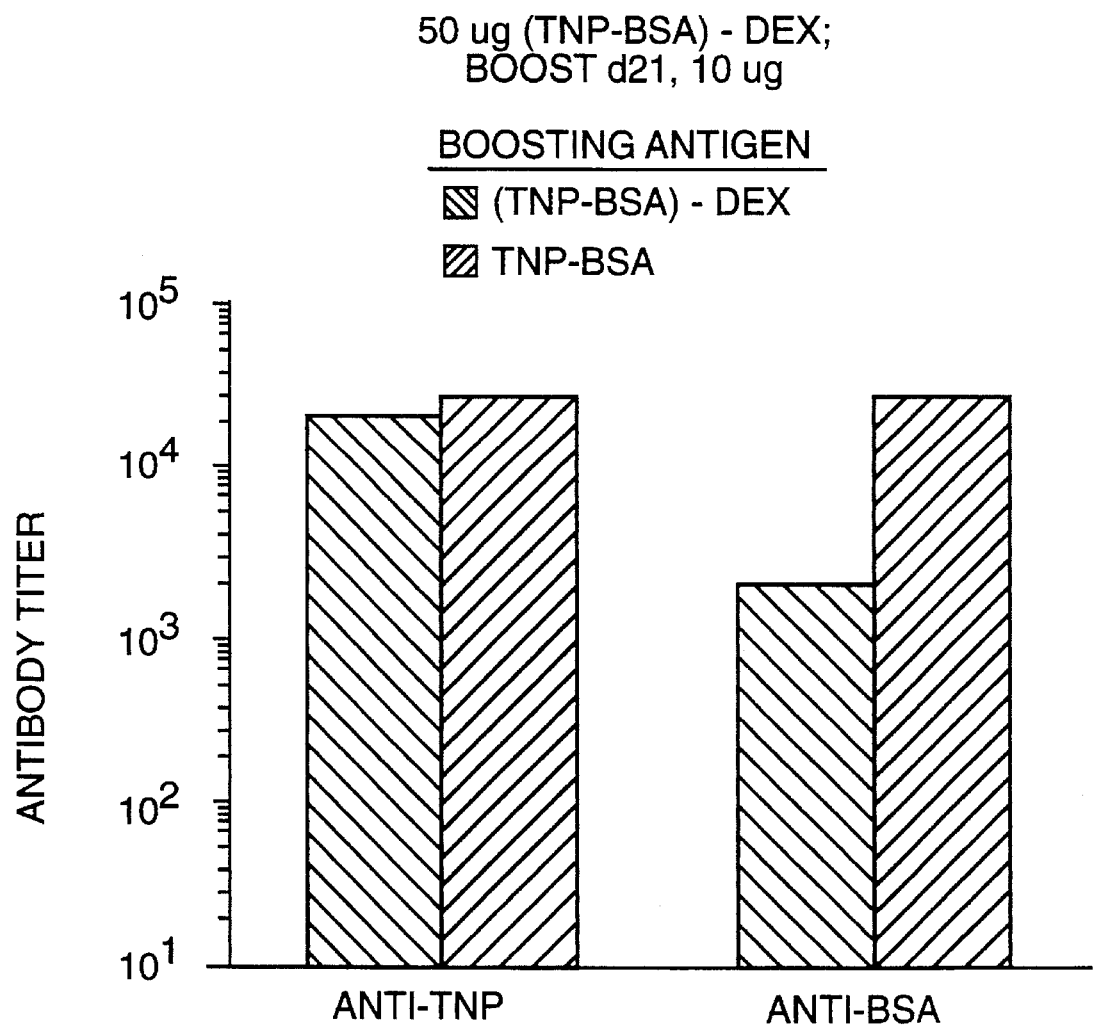

FIG. 8 Graphic representation of the boosting of haptenated BSA-Dex. Mice were immunized with (TNP-BSA) Dex (50 µg) and then boosted with a second injection of either TNP-BSA alone or with TNP-BSA conjugated to Dex. Mice were bled 14 days later and sera titered for anti-TNP and anti-BSA antibody. This figure shows that once mice are immunized with the Dex conjugate (a construct consisting of both primary and secondary carrier), a good booster response is achieved and that antibody boosting can be achieved as effectively with the unconjugated TNP-BSA (secondary carrier only) as with the complete vaccine construct conjugate. This demonstrates that once a primary response has been stimulated with the conjugate, a large secondary response may be elicited by the unconjugated or natural antigen.

Figure 9:
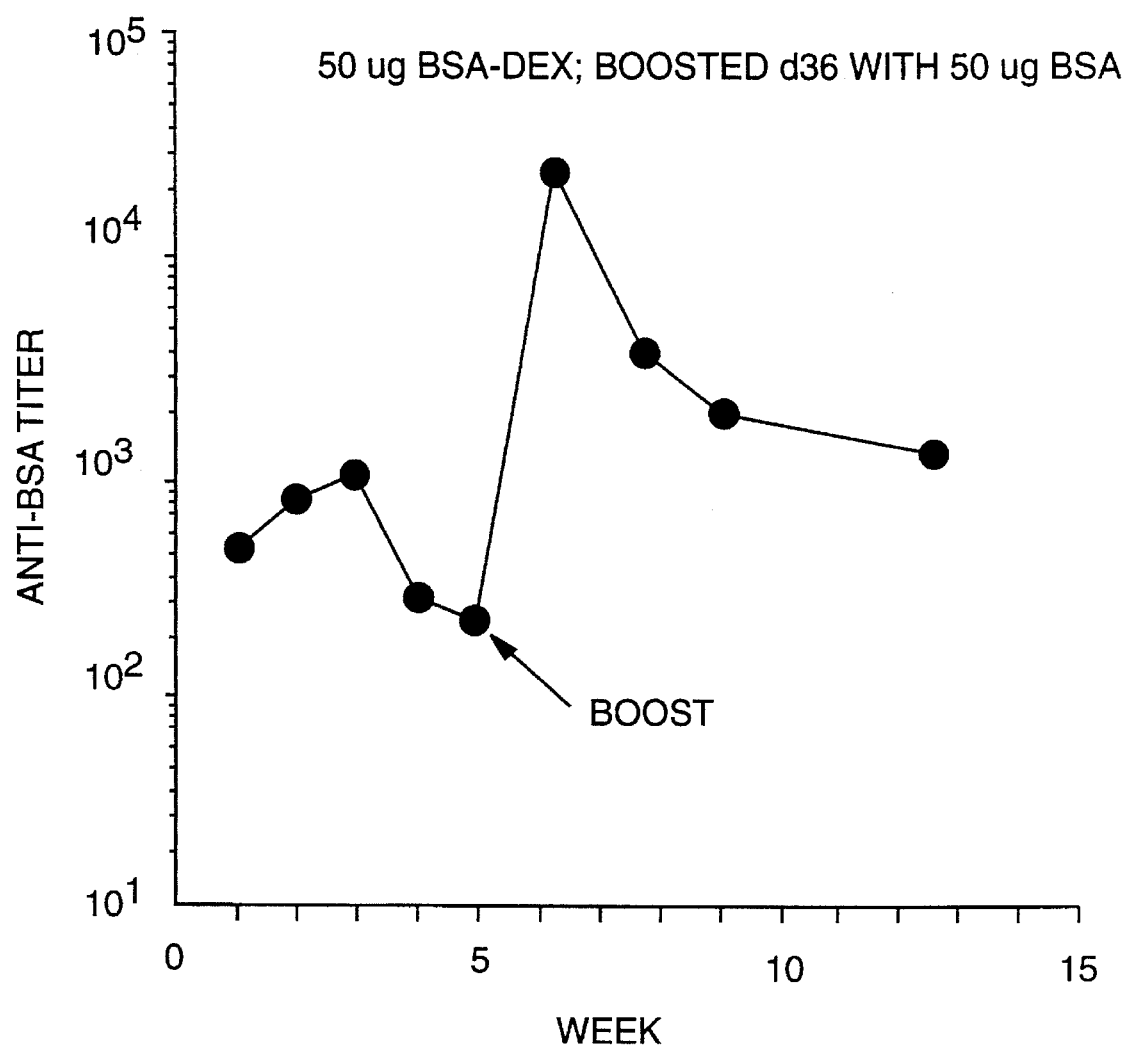

FIG. 9 Graphic representation of the kinetics of BSA-Dex boosted with BSA. Mice were immunized with 50 µg of BSA-Dex (primary and secondary carrier) and 5 weeks later boosted with 50 µg of BSA (secondary carrier only). Mice were bled at various times and sera titered by ELISA for antibody titers to BSA, the secondary carrier. This figure shows that the secondary antibody responses can be elicited by BSA only, the secondary carrier not conjugated to dextran, and that the response is very long-lived and persists for greater than 11 weeks.

Figure 10:
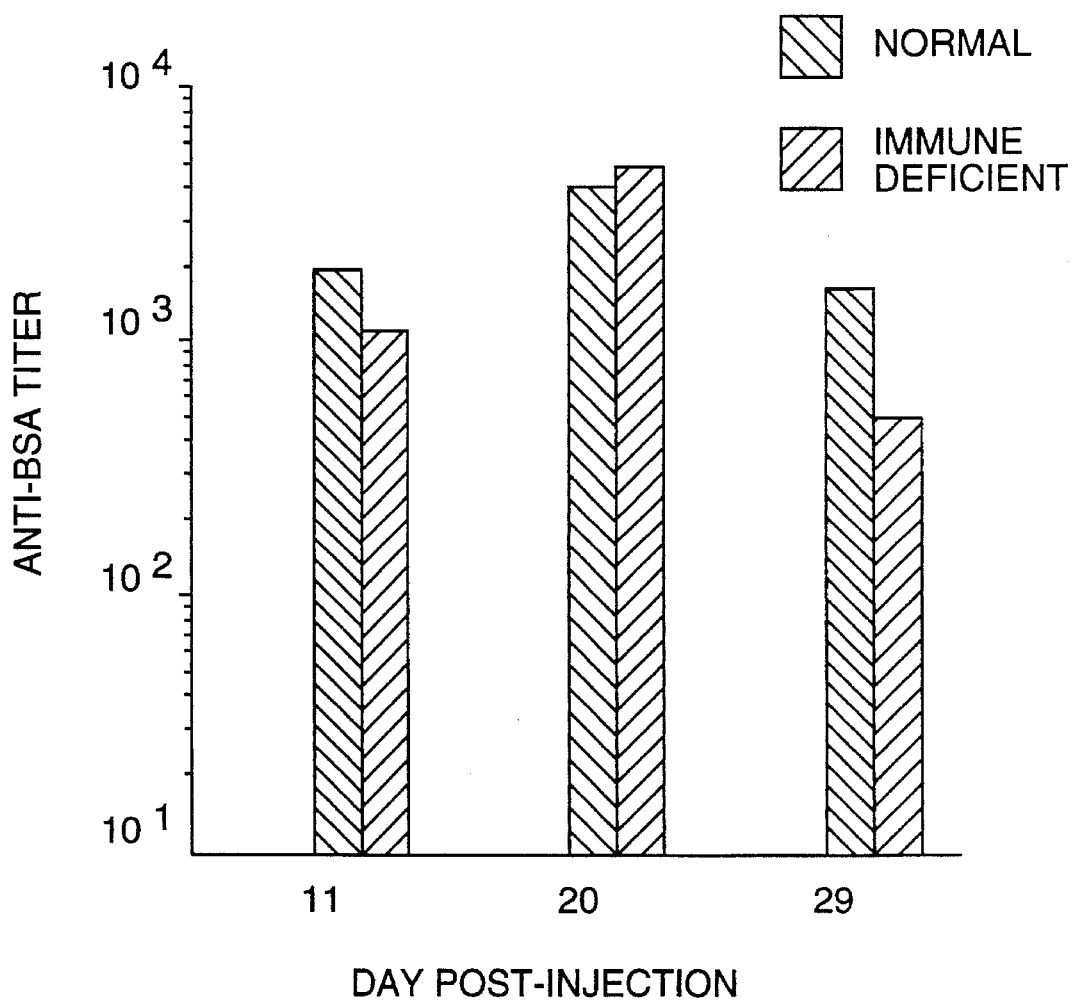

FIG. 10 Graphic representation of antibody response to the carrier. BSA-Dex conjugates (50 µg) were injected into normal or immune defective mice which are unresponsive to Dex. Mice were bled 11, 20 and 29 days later, and sera anti-BSA titers were measured by ELISA. This study demonstrates that the Dex carrier may simply provide a matrix to present antigen to cells in a multivalent array, that the antibody response to the Dex conjugate does not depend on the ability of mice to mount antibody responses to the dextran carrier, that cells of the immune system need not recognize Dex as an immunogen for it to function as an effective carrier, and importantly that the BSA-Dex conjugate can stimulate responses in immune defective mice.

Figure 11:
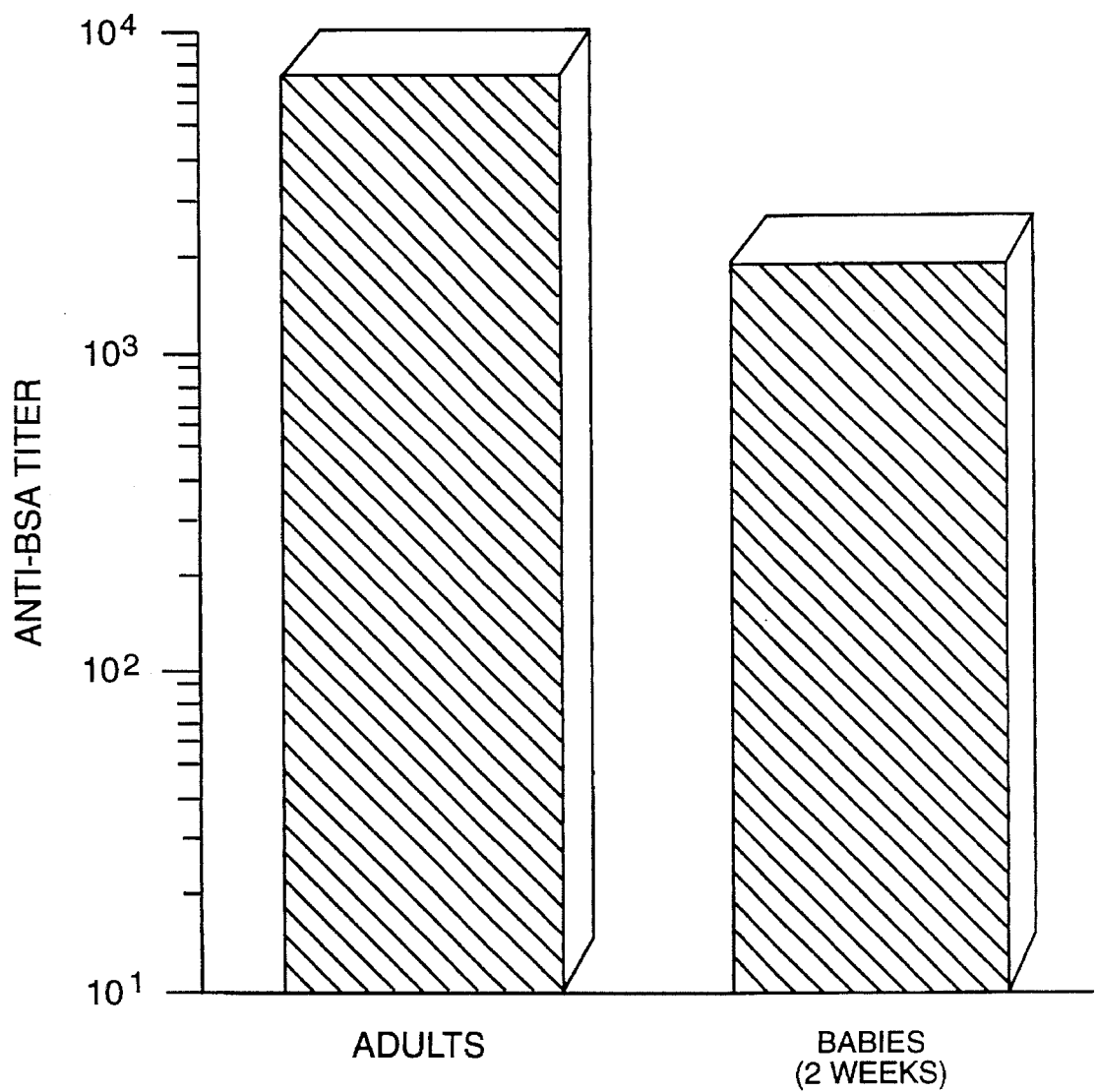

FIG. 11 Graphic representation of the immunogenicity of BSA-Dex in baby mice. Both 2 week old mice and adult mice were injected intraperitoneally with 50 µg of BSA-Dex and bled 12 days later. Sera anti-BSA titers were measured by ELISA. This study shows that even mice that are immunologically immature can be effectively immunized with this Dex protein-carrier conjugate and elicit good antibody responses to the secondary carrier (BSA).

Figure 12:
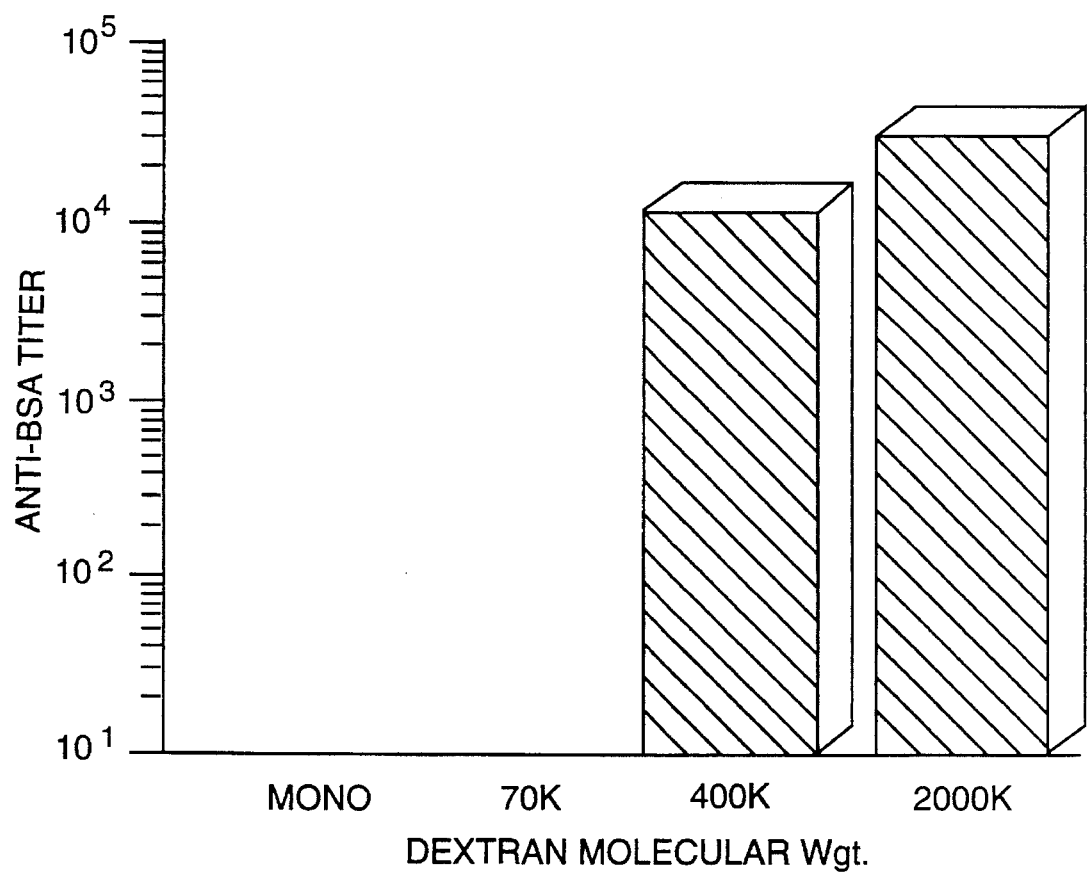

FIG. 12 Graphic representation of the effect of molecular weight. BSA-Dex conjugates were made using size separated Dex of MW 70K, 400K, or 2000K. Mice were injected IV with 50 µg of the various conjugates and bled 14 days later. Serum antibody titers were determined by ELISA. This figure shows that Dex must be >70 KD in size to provide an effective carrier molecule and that, although 400 KD elicits a good response, a larger molecular weight carrier molecule is even more effective.

Figure 13:
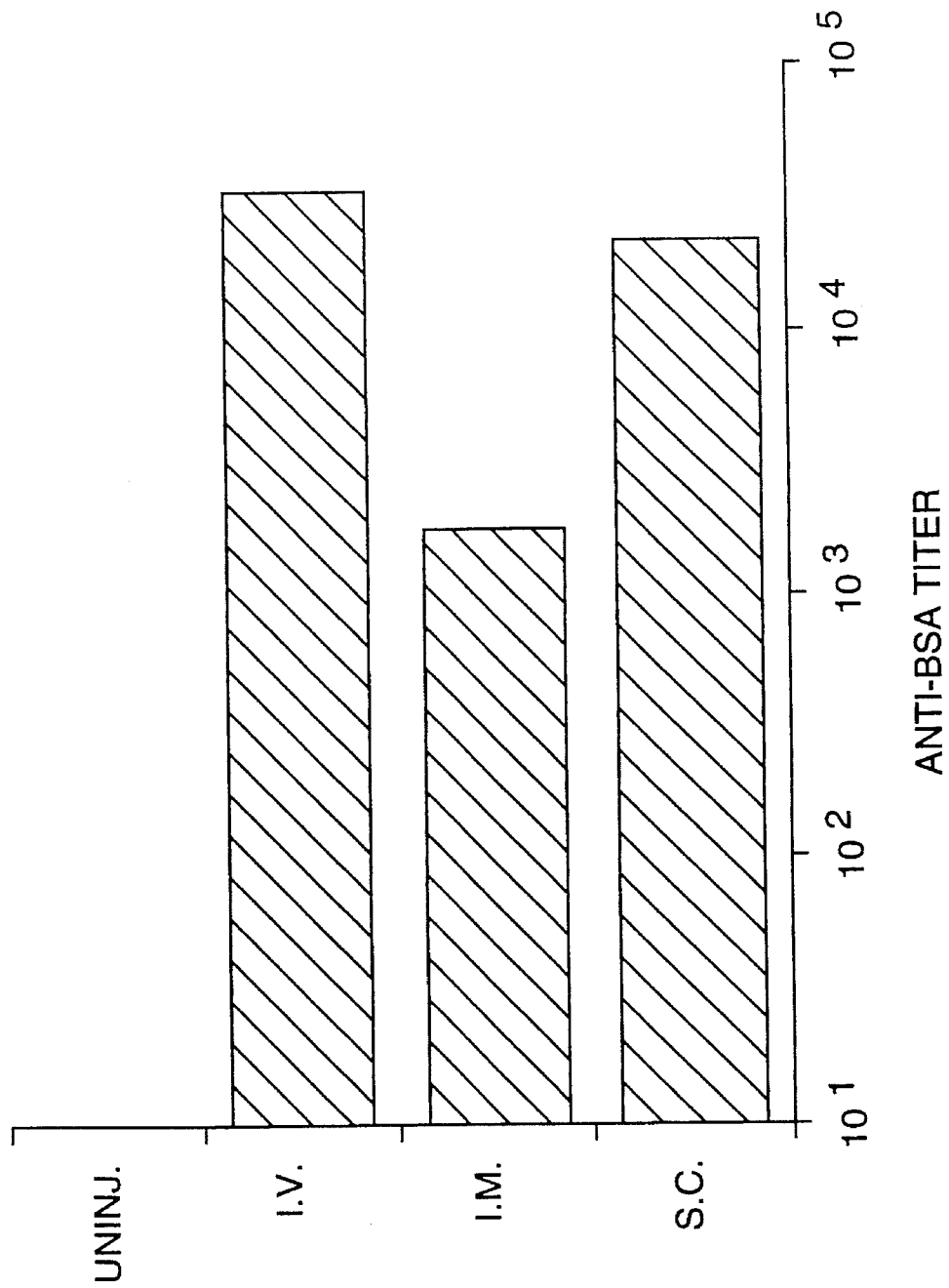

FIG. 13 Graphic representation of the effect of injection mode. Mice were immunized with BSA-Dex via three different routes: intravenously (IV), subcutaneously (SC), or intramuscularly (IM). Mice were bled 14 days later and sera titers determined by ELISA. This study shows that the Dex protein-carrier conjugate (primary and secondary carrier complex) stimulates comparable responses whether given IV, SC or IM.

Figure 14:
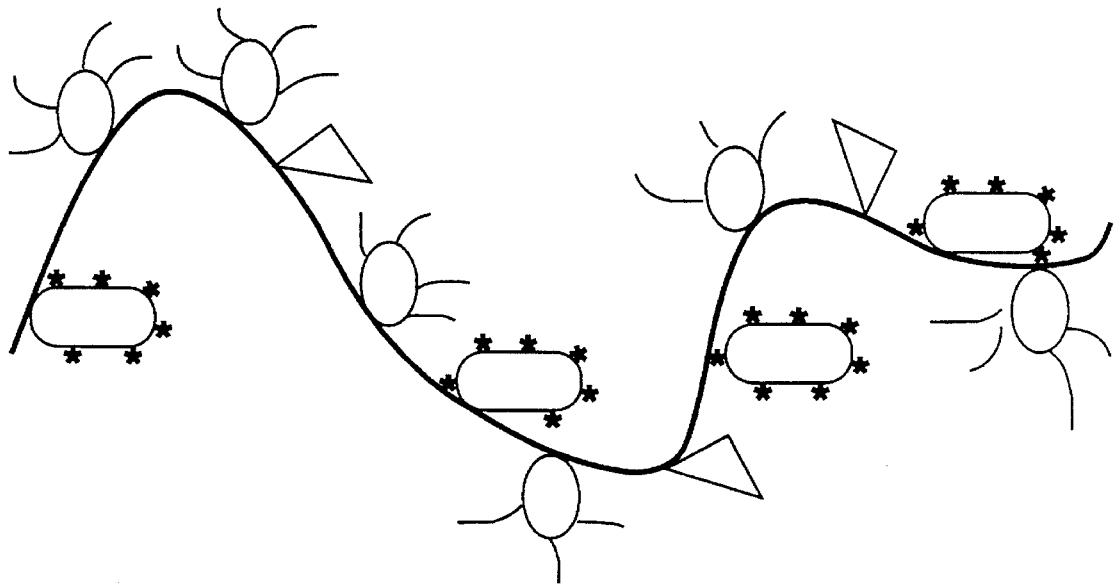
Figure 14:
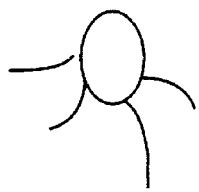
Figure 14:
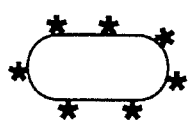
Figure 14:

FIG. 14 Schematic drawing of the dual carrier immunogenic construct to which multiple secondary carriers (tetanus toxoid, meningococcal outer membrane protein, and viral protein) are conjugated to at least one primary carrier. The secondary carriers may or may not be further haptenated.

VI. DETAILED DESCRIPTION OF PREFERRED EMBODIMENTS

Reference will now be made in detail to the presently preferred embodiments of the invention, examples of which are illustrated in the accompanying drawings.

The invention relates to an immunogenic construct made up of at least two carriers, at least one primary carrier that is a large molecular weight molecule of greater than 70 KD molecular weight and a secondary carrier that is a T-dependent antigen conjugated thereto as represented in FIG. 2. A carrier is any substance to which other substances may be attached so that the immunogenicity of the attached substances is enhanced.

In a preferred embodiment, the immunogenicity of the construct is greater than the immunogenicity of at least one carrier alone. Methods of measuring immunogenicity are well known to those in the art and primarily include measurement of serum antibody including measurement of amount, avidity, and isotype distribution at various times after injection of the construct. Greater immunogenicity may be reflected by a higher titer and/or increased life span of the antibodies. Immunogenicity may also be measured by the ability to induce protection to challenge with noxious substances or organisms. Immunogenicity may also be measured by the ability to immunize neonatal and/or immune defective mice. Immunogenicity may be measured in the patient population to be treated or in a population that mimics the immune response of the patient population.

As a result of the contributions of both types of carriers, the dual carrier construct is an extremely potent activator of T cell help via mechanisms such as enhanced antigen presentation by B cells, macrophages or other antigen presenting cells. Such a construct will elicit very rapid and long lived antibody formation in adults, children, and those with immature or immunodeficient immune systems.

The construct of the invention is preferably water soluble or may be maintained in aqueous media. The solubility may derive from the use of solubilizing reagents during the synthesis of the construct. In addition, the construct of the invention may be maintained in aqueous media by the use of solubilizing reagents.

The process of synthesizing the construct of the invention allows one to advantageously control the physical and chemical properties of the final product. The properties that may be controlled include modifying the charge on primary and secondary carriers (an advantage in light of evidence that cationized proteins may be more immunogenic), varying the size of the construct by varying the size of the primary carriers, selecting the degree of crosslinking of the construct (to obtain variations of size and half-life in the circulation), selecting the number of copies of secondary carriers conjugated to primary carriers, and targeting to selected cell populations (such as to macrophages to enhance antigen presentation).

The immune response to the construct of the invention may be further enhanced by the addition of immunomodulators and/or cell targeting moieties. These entities include, for example, (1) detoxified lipopolysaccharides or derivatives, (2) muramyl dipeptides, (3) carbohydrates, lipids, and peptides that may interact with cell surface determinants to target the construct to immunologically relevant cells, (4)

interleukins, and (5) antibodies that may interact with cell surface components.

As represented in FIG. 2, the construct of the invention is made up of at least one primary carrier that provides a large backbone matrix to which one or more copies of secondary carrier may be conjugated. As will be discussed below, one or more primary or secondary carriers may be further conjugated to moieties. Methods of conjugation are well known to those of ordinary skill in the art, and include the heteroligation techniques of Brunswick M., et al., J. Immunol. 140:3364 (1988), specifically incorporated herein by reference. See also Wong, S. S. Chemistry of Protein Conjugates and Crosslinking CRC Press, Boston (1991), specifically incorporated herein by reference. The conjugation of carriers within this invention may provide minimal disruption of critical epitopes on the carriers, since protein conjugation to a carrier, such as dextran, involves minimal alterations to the dextran.

A primary carrier within the invention may also include functional groups or, alternatively, may be chemically manipulated to bear functional groups. The presence of functional groups may facilitate covalent conjugation of a primary carrier to one or more secondary carriers. Such functional groups include, but are not limited to, amino groups, carboxyl groups, aldehydes, hydrazides, epoxides, and thiols.

The large backbone of each primary carrier provides an ideal matrix for many different secondary carriers so that one vaccine could contain multiple antigenic specificities. Moreover, the primary carrier stimulates antibody production by presenting numerous copies of secondary carriers at a relatively high antigenic density to both B and T cells. It may also provide other advantages including targeting of the construct to macrophages or other cell types to enable enhanced antigen processing.

In a preferred embodiment, the molecular weight of at least one primary carrier ranges from greater than 70,000 to 2,000,000 KD and above. As set forth in FIG. 12, a more preferred molecular weight is 400,000 KD and above, and an even more preferred molecular weight is 2,000,000 KD. The conjugation of the primary carrier to at least one secondary carrier may result in crosslinking of the primary carrier. Such crosslinking may permit the use of lower molecular weight carriers (such as 70,000 KD) so long as the final construct is of a higher molecular weight. Based on the teachings contained herein together with the ordinary skill in the art, the skilled artisan will know how to select the optimum molecular weight for the particular construct desired.

In another preferred embodiment, at least one primary carrier is a T-independent antigen, thereby combining the advantages of T-independent and T-dependent antigens. Such a carrier that can itself directly and potently activate B cells and can serve as a large but relatively nondegradable backbone to carry many secondary carriers. As detailed below, however, the invention may be practiced, however, with a primary carrier that is not immunogenic by itself.

A primary carrier may be naturally occurring, a semisynthetic or a totally synthetic large molecular weight molecule. In a preferred embodiment, at least one primary carrier is a polymer selected from the group consisting of dextran, carboxymethyl cellulose, agarose, pneumococcal type III polysaccharide, ficoll, polyacrylamide, and combinations thereof. In the most preferred embodiment, the primary carrier is a dextran. As used herein, dextran ("dex") refers to a polysaccharide composed of a single sugar and may be obtained from any number of sources, including Pharmacia. Ficoll, an example of a semi-synthetic polymer, is an inert synthetic non-ionized high molecular weight polymer. Synthetic polymers include polyacrylamide (a water-soluble high molecular weight polymer of acrylic resin), poly (lactide-co-glycolide), polyvinyl alcohol, partially hydrolyzed polyvinyl acetate, and polyvinylpyrrolidine.

The secondary carrier of this construct also provides specific advantages for eliciting good antibody responses. As a T-dependent antigen, the secondary carrier can activate and recruit T cells and thereby augment T cell dependent antibody production. The secondary carrier need not, however, be strongly immunogenic by itself, although strongly immunogenic carriers are within the scope of this invention. Coupling of multiple copies of the secondary carrier to the primary carrier significantly augments antibody production against the secondary carrier even in the absence of adjuvants.

In a preferred embodiment, the secondary carrier is a protein, a peptide, a T cell adjuvant or any other compound capable of activating and recruiting T cell help. The protein may be selected from a group consisting of but not limited to viral, bacterial, parasitic, animal and fungal proteins. In a more preferred embodiment, the secondary carrier is albumin (such as bovine serum albumin), tetanus toxoid, diphtheria toxoid, or bacterial outer membrane protein, all of which may be obtained from biochemical or pharmaceutical supply companies or prepared by standard methodology (Cruse, J. M. (ed.) Conjugate Vaccines in Contributions to Microbiology and Immunology vol. 10 (1989), specifically incorporated herein by reference). Other proteins that could function as secondary carriers would be known to those of ordinary skill in the art of immunology.

The secondary carriers of the invention are capable of being conjugated to at least one primary carrier. The secondary carriers may either contain functional groups that can react with the primary carriers or the secondary carriers may be chemically manipulated to be capable of reacting with the primary carriers discussed above.

As described above, numerous copies of specific secondary carriers as well as a variety of secondary carriers may be conjugated to the primary carrier. Coupling of multiple copies of the secondary carrier to the primary carrier significantly augments antibody production to the secondary carrier.

The secondary carriers of the invention are preferably water soluble, whether conjugated or unconjugated or whether coupled to the immunogens discussed below.

In another embodiment, moieties may be further conjugated to one or more of the primary and/or secondary carriers, as represented in FIG. 2. Such conjugation promotes enhanced antibody responses to the moiety. Techniques to conjugate such moieties to either the primary or secondary carriers are well known to those skilled in the art, and include, in part, coupling through available functional groups (such as amino, carboxyl, thio and aldehyde groups). See S. S. Wong, Chemistry of Protein Conjugate and Crosslinking CRC Press (1991), and Brenkeley et al., Brief Survey of Methods for Preparing Protein Conjugates With Dyes, Haptens and Cross-Linking Agents, Bioconjugate Chemistry 3 #1 (Jan. 1992), specifically incorporated herein by reference.

As used herein, moiety is any substance that is able to stimulate the immune system either by itself or once coupled. Moieties include haptens, antigens, or combinations thereof. Haptens refer to small molecules, such as chemicals, dust, and allergens, that by themselves are not able to elicit an antibody response, but can once coupled to a carrier. An antigen is any molecule that, under the right circumstances, can induce the formation of antibodies. These haptens and antigens may derive from but are not limited to bacteria, rickettsiae, fungi, viruses, parasites, drugs, or chemicals. They may include, for example, small molecules such as peptides, oligosaccharides (for example the polyribosyl-ribitol-phosphate of *H. influenzae*), toxins, endotoxin, etc.

In another embodiment, the invention relates to vaccines that are made up of the dual carrier immunogenic construct together with a pharmaceutically acceptable carrier. Such vaccines will contain an effective therapeutic amount of the dual carrier immunogenic construct together with a suitable amount of carrier so as to provide the form for proper administration to the patient.

Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are described in Martin, E. W., Remington's Pharmaceutical Sciences, specifically incorporated herein by reference.

The vaccines that may be constructed from the dual carrier immunogenic construct of the invention may include, but are not limited to, the vaccines set forth in Chart 1.

Chart 1

Diphtheria vaccine
Pertussis (subunit) vaccine
Tetanus vaccine
*H. influenzae*, type b (polyribose phosphate)
*S. pneumoniae*, all serotypes
*E. coli*, endotoxin or J5 antigen (LPS, Lipid A and Gentabiose)
*E. coli*, O polysaccharides (serotype specific)
Klebsiella, polysaccharides (serotype specific)
*S. aureus*, types 5 and 8 (serotype specific and common protective antigens)
*S. epidermidis*, serotype polysaccharide I, II and III (and common protective antigens)
*N. meningiditis*, serotype specific or protein antigens
Polio vaccine
Mumps, measles, rubella vaccine
Respiratory Syncytial Virus
Rabies
Hepatitis A, B, C, and others
Human immunodeficiency virus I and II (GP120, GP41, GP160, p24, others)
Herpes simplex types 1 and 2
CMV
EBV
Varicella/Zoster
Malaria
Tuberculosis
*Candida albicans*, other candida
*Pneumocystis carinii*
Mycoplasma
Influenzae virus A and B
Adenovirus
Group A *streptococcus*
Group B *streptococcus*, serotypes, Ia, Ib, II and III
*Pseudomonas aeruginosa* (serotype specific)
Rhinovirus
Parainfluenzae, types 1, 2 and 3
Coronaviruses
Salmonella
Shigella
Rotavirus Chart 1-continued Enteroviruses
*Chlamydia trachomatis & pneumoniae* (TWAR)

The invention also relates to the treatment of a patient by administration of an immunostimulatory amount of the vaccine. Patient refers to any subject for whom the treatment may be beneficial and includes mammals, especially humans, horses, cows, dogs, and cats as well as other animals, such as chickens. An immunostimulatory amount refers to that amount of vaccine that is able to stimulate the immune response of the patient for the prevention, amelioration, or treatment of diseases. The vaccine of the invention may be administered by any route, but is preferably administered by intravenous, intramuscular, and subcutaneous injections.

The invention also relates to a method of preparing an immunotherapeutic agent against infections caused by bacteria, viruses, parasites, fungi, or chemicals by immunizing a host with the vaccine described above so that the donor produces antibodies directed against the vaccine. Antibodies would be isolated or B cells may be obtained to later fuse with myeloma cells to make monoclonal antibodies. The method of making monoclonal antibodies is well known in the art, Kohler and Milstein Nature 256:495 (1975), specifically incorporated herein by reference, and needs no further description here. As used herein, immunotherapeutic agent refers to a composition of antibodies that are directed against specific immunogens for use in passive treatment of patients. A plasma donor is any subject that is injected with a vaccine for the production of antibodies against the immunogens contained in the vaccine.

The invention also relates to a method of treating a patient by the administration of a protective amount of the immunotherapeutic agent. Such a treatment is passive in that it does not call on the patient to produce antibodies against an immunogen, but rather uses antibodies produced by the plasma donor against the immunogen. The amount of therapeutic antibodies is protective if it presents a sufficient number of antibodies that can prevent, ameliorate, or treat the disease caused by the immunogen. Such an amount may be determined by those of ordinary skill in the art and varies based on the characteristics of the patient and the disease profile.

The invention also relates to a method of producing a diagnostic and/or research reagent to detect agents that are characteristic of diseases caused by, for example, bacteria, viruses, fungi, parasites or chemicals by immunizing a host with a vaccine described above so that the host produces antibodies (or B cells) against the agents. The antibodies and/or B cells may be isolated as described above. As used herein, diagnostic reagent refers to a composition of antibodies (polyclonal or monoclonal) that may be used to detect agents that are characteristic of diseases. As used herein, research reagent refers to a composition of antibodies (polyclonal or monoclonal) that may be used in the laboratory.

The herein offered examples provide methods for illustrating, without any implied limitation, the practice of this invention in the production of vaccines to produce antibodies either monoclonal or polyclonal, which could be employed for active or passive prophylaxis or therapy, and for diagnostic, or research purposes.

The profile of the representative experiments have been chosen to illustrate methods for producing a novel dual carrier vaccine and the concepts of function.

METHODS

I. Mice (DBA/2J) were used at 8 weeks old unless otherwise noted and were immunized with 0.1 ml and a saline solution of various antigens intravenously, subcutaneously, or intramuscularly. In all experiments 5 mice per group were used. Bleeding was by tail vein.

II. Amino ethyl carbamyl Dex (AECM Dex)

Amino-ethyl carbamyl dextran (AECM Dex) was prepared essentially as described by Brunswick et al., J. Immunol. 140:3363 (1988), specifically incorporated herein by reference. AECM T2000 dextran (Pharmacia) was passed over a gel permeation column (CL2B column 2.5×105 cm). Material from the from the first third of the column was pooled and determined to have an average molecular weight of 2,000,000 daltons. This material is now referred to as HMW AECM Dextran. AECM dextrans were also prepared from T70 and T500 dextran (Pharmacia) and fractionated on CL6B and CL4B columns, respectively. A center cut was taken, concentrated and rerun to obtain a relatively homogenous preparation. Trinitrobenzene sulfonic acid (TNBS) was used to determine the average number of amino groups per dextran molecule. High molecular weight dextran preparations had from 150 to 200 amino groups per 2,000,000 daltons. The AECM T500 preparation had an average of 150 amino groups per 400,000 daltons and the AECM T70 preparation had an average of 35 amino groups per 70,000 daltons. In order to facilitate the determination of dextran concentrations, AECM dextran was routinely radiolabelled by reaction with a small amount of N-succinimidy [3H-2.3] propionate (Amersham) [3H-NSP]. Approximately one in 10,000 dextran molecules were modified. (3H-AECM HMW Dex) was lightly trinitrophenylated as follows: 50 ul of 0.01M freshly prepared TNBS in 0.01M sodium borate pH 9.3 was added to a stirred solution of 20 mg of HMW AECM-Dex in 2 ml HEPES buffer plus 0.5 ml 0.1M sodium borate buffer pH 9.3. After 2 hours in the dark at room temperature, reagents were removed on P6DG desalting column (BioRad) and the labeled dextran concentrated by ultrafiltration using a Centricon 30 (Amicon). Using a molar extinction coefficient of 11,000 at 366 nm, the ratio of TNP to HMW dextran was determined to be 40:1. This left approximately 100–150 free amino groups for further reaction.

III. Conjugation of proteins to AECM Dex

Proteins were conjugated to the AECM dextran using heteroligation techniques (Brunswick M, et al., J. Immunol. 140:3364, 1988, specifically incorporated herein by reference). Protein was acetylthiolated and the dextran iodoacetylated with the reagent SIAP (Brunswick M, et al., J. Immunol. 140:3364, 1988, specifically incorporated herein by reference) but other reagents such as iodoacetic acid n-hydroxy succinimide ester (IANHS) could be used.

Proteins were typically reacted with 4–8 fold molar excess of SATA (Calbiochem) for 1–2 hours. The activated dextrans and protein were each desalted into Acetate buffer (10 mM NaAcetate, 0.1M NaCl, 2 mM EDTA, 0.02% SodiumAzide, pH 5.0) to remove excess reagent and concentrated using a Centricon 30. Protein and dextran were typically mixed at molar ratios of 30–60:1, the pH raised to 7.5 with HEPES buffer+hydroxylamine. The final concentrations were 75 mM HEPES, 2 mM EDTA, 0.02% azide and 50 mM hydroxylamine. After an overnight reaction at 4° C., the conjugate was treated with 0.2 mM mercaptoethanol for 1 hour (to consume any remaining iodoacetyl groups) followed by 10 mM iodoacetamide (to consume all thiol groups), further concentrated if necessary, and passed over a 1×58 cm gel filtration column, equilibrated with PBS, containing S200SF, S300SF or S400SF (Pharmacia), depending on the molecular weight of the protein. The radioactive void column peak was pooled and concentrated if necessary. Solutions were sterilized by passage through a Millex GV or HV filter (Millipore).

P74 peptide (Cys-Asa-Ile-Gly-Lys-Val-Pro-Asa-Val-Gln-Asp-Gln-Asn-Lys)(SEQ ID NO:1) was conjugated to BSA as follows. 11.6 mg BSA (Pentex) in 400 ul HEPES buffer was made 10 mM in iodoacetamide. This was to block any native thiol groups which might react with the heterobifunctional reagent and cause polymerization. After a 10 minute incubation, the protein was iodoacetylated by adding a 12-fold molar excess of IANHS. After one hour, the solution was desalted into acetate buffer and concentrated to 39 mg/ml.

The thiol peptide was radiolabeled so that the amount to peptide conjugated to BSA could be estimated. The peptide was dissolved in HEPES buffer and a 1.5 fold molar excess of Ellman's reagent was added to block the thiol. After 30 minutes, a 10 fold molar excess of N-ethyl maleimide was added to consume thiols of the half-Ellman's reagent released. 1 hour later the thiol protected peptide was radiolabeled with N-succinimidyl [$^3$H-2,3]-propionate ($^3$H-NSP) (Amersham). Just before conjugation, the peptide solution was made 50 mM dithiothreitol and all reagents removed on a 1×38 cm G-10 column (Pharmacia). The radioactive peak running in the void volume was pooled. The specific activity of the peptide was about $2.5 \times 10^{11}$ cpm/mole. The radiolabeled thiol peptide was added to 4.5 mg iodoacetylated BSA at a molar ratio of 15:1 and the pH raised to 7.5 by the addition of 5×HEPES buffer. The final volume was 1.2 ml. After an overnight reaction, the solution was treated with 0.2 mM mercaptoethanol for 1 hour and the unreacted peptide removed on a 1×15 cm P6DG column equilibrated with PBS. The final peptide BSA ratio was determined to be 6:1. This peptide-protein conjugate was then coupled to dextran as described for BSA.

B-lactoglobulin B, aprotinin, ovalbumin (OVA) and lysozyme were obtained from Sigma. Bovine serum albumin (BSA) was from Pentex or Amresco (Biotech grade). Vaccinia protein was the generous gift of Dr. Isabella Quarkyi (Georgetown University Medical School).

TNP-OVA and TNP-BSA was prepared by adding a 4–12 fold molar excess (from a 0.25M stock) of TNBS in 0.1M NaBorate, 0.2M NaCl, 0.02% NaAzide, pH9.1) to a 50 mg/ml solution of OVA or BSA respectively in the same buffer. After an overnight reaction at 4° C., the protein was dialyzed into HEPES buffer. The ratio was determined from the OD at 366 nm and correcting the hapten contribution at 280 nm. (OD280=0.32×OD 366).

IV. Serum IgGl, and IgM anti-TNP titers were determined by and ELISA. This assay was performed similarly to our previously described assay, except in this case we used alkaline phosphate conjugated antibodies and microtiter wells were coated for 2 hours with 10 μg/ml of TNP Ficoll for measuring anti TNP antibodies or with 10 μg/ml of BSA for measuring anti-BSA antibodies. Following treatment with alkaline phosphate-conjugated antibodies, microtiter plate wells were filled with 200 μl of p-nitrophenyl phosphate (1 mg/ml in 1M Tris, pH 9.8), incubated for ½ to 1 hour at room temperature, and the $A_{405}$ of the solution in each well was determined with a Titertek Multiskan Spectrophotometer (Flow Laboratories, McLean, Va.). The titers for the ELISA were calculated as previously described (See Current Protocols in Immunology, Vol. I, ed. J. Coligan, A. Kruisbeck, D. Margulies, E. Shevach and W. Strober. J. Wiley & Sons, 1991, specifically incorporated herein by reference).

EXAMPLE 1

Current vaccines have many deficiencies that include poor immunogenicity, the need for separate vaccine constructs for each antigen and the requirement for multiple booster injections to elicit good antibody production. A high molecular weight polymer (HMWP) was utilized as a primary antigen carrier to provide the vaccine backbone. While any HMWP could be used, Dex was the choice for these studies. The Dex HMWP was used to provide a high density presentation of the secondary carrier to T cells and B cells and to provide a carrier for many other different antigens (FIGS. 1 & 2).

When antigens are coupled to the HMWP primary carrier the antibody response to these antigens is enhanced (FIGS. 3 and 4). While a single injection of unconjugated BSA elicits no detectable antibody response, BSA conjugated to Dex elicits a good antibody response at 10–500 μg/dose (FIG. 3). Conjugation of different proteins to Dex, the primary carrier, makes them strongly immunogenic (FIG. 4). These studies included viral antigens (Vaccinia-Dex), bacterial antigens and toxins (Cholera toxin-Dex) and other substances that were poorly immunogenic. Therefore, a secondary protein carrier could include a wide variety of proteins such as BSA or toxins/toxoids such as cholera, tetanus or diphtheria. The molecular weight of the Dex primary carrier can vary, but must be >70 KD and is a most effective carrier molecule at about 400 and 2000 KD) in size (FIG. 12). However, the optimal size for the HMWP may vary depending on the specific primary carrier utilized. The Dex HMWP is a polysaccharide and immune defective mice do not mount antibody responses to it. However, both normal and immune defective mice produce equally good antibody responses to BSA coupled to Dex (FIG. 10). This demonstrates that Dex as a primary carrier simply provides a matrix to present antigen(s) to cells in a multivalent array and itself need not be immunogenic. These studies also show that a variety of proteins could be used as secondary carriers and that the secondary carrier could serve both as a vaccine antigen and a carrier for non-immunogenic antigens.

EXAMPLE 2

The dual carrier vaccine construct is demonstrated fully using TNP (FIG. 5). Mice are immunized with TNP coupled to the secondary carrier BSA (TNP-BSA) and TNP-BSA is also coupled to the HMWP primary carrier (Dex). Conjugation of TNP to the secondary carrier BSA alone did not enhance the antibody response to TNP. However, coupling the secondary carrier/TNP complex to the primary carrier to provide [(TNP-BSA)-Dex] enhanced the immunogenicity of TNP. In addition BSA (the secondary carrier) was immunogenic when coupled with Dex alone or with Dex and TNP. Therefore using the dual carrier vaccine construct, a HMWP can carry the secondary carrier and other antigens may be coupled to the secondary carrier. Antibodies will be elicited to the secondary carrier as well as the antigen conjugated to it and non-immunogenic haptenic molecules will be rendered immunogenic. This could be particularly important if the secondary carrier is an antigen to which antibody would provide protective immunity, such as tetanus or diphtheria toxoid. This vaccine construct also allows multiple unrelated antigens to be conjugated to the primary carrier (FIG. 7). TNP was coupled to OVA (the secondary carrier) and then conjugated to Dex (the primary carrier). LYS was also independently conjugated directly to Dex. Antibodies were elicited to each of the antigens. Thus the HMWP backbone of this vaccine construct is suitable for producing multivalent vaccines with an array of secondary carrier proteins and or many different antigens coupled to the secondary carrier. (multicarrier/multiantigen vaccine)

EXAMPLE 3

In the previous examples the dual carrier vaccine construct was shown to be effective with a variety of antigens. This data is supported and extended using a parasitic (malarial) derived peptide antigen (p74, SEQ ID NO:1). The dual carrier vaccine construct was shown to be significantly better than peptide antigen alone or peptide conjugated to the secondary carrier BSA (FIG. 6). A good antibody response was elicited to this small antigen only after the P74-BSA conjugate was coupled to the HMWP primary carrier (Dex). However, the HMWP carrier simply provides a matrix to present antigens to cells and need not be immunogenic (FIG. 10).

EXAMPLE 4

For a vaccine to effectively enhance immunity over a long period of time, a good booster response is important. After a primary immunization with the dual carrier vaccine, a booster antibody response can be elicited even with the unconjugated secondary carrier (FIG. 8). Furthermore, when a haptenated carrier was employed a booster response was observed to both the TNP and to the BSA secondary carrier. Further analysis shows that the primary and secondary antibody response to the BSA secondary carrier is long lived (FIG. 9).

EXAMPLE 5

The BSA-Dex conjugate was analyzed to evaluate the effect of host immune status and route of immunization on antibody response. Both immunologically mature adult and immunologically immature baby mice were effectively immunized with the primary and secondary carrier complex demonstrating that the dual carrier vaccine will elicit an antibody response even in babies and young infants with immature immunity (FIG. 11). The antibody response to BSA (the secondary carrier) is similar in both the adult and baby mice. In addition IV, IM, and SC routes all elicited a good antibody response to BSA (FIG. 13). The route of administration of vaccine is not limited therefore to any single type of inoculation and it is not limited by the age or immunologic status of the vaccine recipient. However, the size of the HMWP is critical to provide an effective vaccine construct. For example for the HMWP Dex the size must be >70,000D, preferably >400,000D (FIG. 12).

EXAMPLE 6

The preparation of a multiple carrier vaccine is illustrated in FIG. 14. Three secondary carriers are employed in this system, two of which are further conjugated to another moiety. *H. influenzae* PRP is coupled to a tetanus toxoid secondary carrier, a malarial derived peptide is coupled to a meningococcal outer membrane protein, and a viral protein (such as RSV-F protein) is left unconjugated. One or more of each of the secondary carriers is then conjugated to the high molecular weight polymer backbone.

EXAMPLE 7

A vaccine can be designed to bear multiple specificities under any of the following four approaches:

(1) Two or more constructs, each consisting of different secondary carriers conjugated to the same primary carriers;

(2) Two or more different constructs, each consisting of the same primary and secondary carrier but different moieties;

(3) Two or more different constructs, each consisting of different primary carriers, the same secondary carriers, and different moieties; and (4) Two or more different constructs, each consisting of different primary and secondary carriers and different moieties.

EXAMPLE 8

As set forth in Charts 2 and 3 below, immunization with dextran-conjugated to TNP-BSA greatly enhanced many parameters of the antibody response, including magnitude, persistence of response etc. (Chart 2). Similarly, immunization with BSA-dextran or TNP-BSA dextran greatly enhanced many parameters of the antibody response (Chart 3).

Chart 2

Comparison of antibody responses elicited by TNP-dextran and BSA-dextran or TNP-BSA dextran immunized with:

| | TNP-BSA (no adjuvant) anti-TNP titers | TNP-BSA dextran |
|---|---|---|
| A. Magnitude response | − | ++++ |
| B. Persistence response | − | ++++ |
| C. Ability to boost for secondary response | − | ++++ |

Chart 2-continued

Comparison of antibody responses elicited by TNP-dextran and BSA-dextran or TNP-BSA dextran immunized with:

| | TNP-BSA (no adjuvant) anti-TNP titers | TNP-BSA dextran |
|---|---|---|
| D. Ability to immunize neonate | − | ++++ |
| E. Ability to immunize B cell defective mice | − | ++++ |
| F. Antibody activity | − | ++++ |
| G. Ability to immunize subcutaneously | − | ++++ |

Chart 3

Comparison of antibody responses elicited by TNP-dextran, BSA-dextran or TNP-BSA dextran immunized with:

| | TNP-dextran anti-TNP titer | BSA-dextran or TNP-BSA dextran anti TNP or BSA titer |
|---|---|---|
| A. Magnitude response | + | ++++ |
| B. Persistence response | 7–10 d | 40–60 d |
| C. Ability to boost for secondary response | − | ++++ |
| D. Ability to immunize neonate | − | ++++ |
| E. Ability to immunize B cell defective mice | − | ++++ |
| F. Antibody activity | LOW | High |
| G. Ability to immunize subcutaneously | + | ++++ |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A dual carrier immunogenic composition, comprising
at least one primary carrier and at least one secondary carrier,
wherein said primary carrier is a molecule having a molecular weight equal to or greater than 2000 kDa and having T-independent antigen characteristics, said secondary carrier is a T-dependent antigen and is chemically conjugated to said primary carrier,
wherein the composition enhances an antibody response to the primary carrier and to the secondary carrier.

2. The dual carrier immunogenic composition of claim 1, wherein at least one primary carrier is selected from the group consisting of dextran and a microbial polysaccharide.

3. The dual carrier immunogenic composition of claim 2, wherein at least one primary carrier is dextran.

4. The dual carrier immunogenic composition of claim 2, wherein at least one primary carrier is a microbial polysaccharide.

5. The dual carrier immunogenic composition of claim 4, wherein at least one primary carrier is *H. influenzae* type b polyribosyl-ribitol-phosphate.

6. The dual carrier immunogenic composition of claim 4, wherein at least one primary carrier is a pneumococcal capsular polysaccharide.

7. The dual carrier immunogenic composition of claim 1, wherein at least one secondary carrier is a protein or a peptide.

8. The dual carrier immunogenic composition of claim 7, wherein the protein or peptide is selected from the group consisting of viral, bacterial, parasitic, animal and fungal proteins or peptides.

9. The dual carrier immunogenic composition of claim 8, wherein the protein or peptide is selected from the group consisting of diphtheria toxoid, pertussis toxoid, tetanus toxoid, bacterial outer membrane protein, viral outer membrane protein, and combinations thereof.

10. The dual carrier immunogenic composition of claim 1, wherein at least one primary carrier is chemically conjugated to a plurality of one or more secondary carriers.

11. The dual carrier immunogenic composition of claim 1, further comprising an adjuvant.

12. A vaccine, comprising:
an immunostimulatory amount of at least one of the dual carrier immunogenic compositions of claim 1, and
a pharmaceutically acceptable carrier.

13. A method of treating a patient, comprising administering to the patient the vaccine of claim 12.

14. The method of claim 13, wherein the vaccine is administered intravenously, intramuscularly, or subcutaneously.

15. A dual carrier immunogenic composition, comprising:
at least one primary carrier comprising a molecule having a molecular weight equal to or greater than 2000 kDa and having T-independent antigen characteristics;
at least one secondary carrier comprising a T-dependent antigen chemically conjugated to the primary carrier; and
at least one moiety,
wherein said moiety, being other than the secondary carrier, is selected from the group consisting of haptens, antigens, and combinations thereof, and conjugated to either a primary carrier or a secondary carrier;
wherein the composition enhances an antibody response to the primary carrier, to the secondary carrier, and to the moiety.

16. The dual carrier immunogenic composition of claim 15, wherein at least one primary carrier is selected from the group consisting of dextran and a microbial polysaccharide.

17. The dual carrier immunogenic composition of claim 16, wherein at least one primary carrier is dextran.

18. The dual carrier immunogenic composition of claim 16, wherein at least one primary carrier is a microbial polysaccharide.

19. The dual carrier immunogenic composition of claim 18, wherein at least one primary carrier is *H. influenzae* type b polyribosyl-ribitol-phosphate.

20. The dual carrier immunogenic composition of claim 18, wherein at least one primary carrier is a pneumococcal capsular polysaccharide.

21. The dual carrier immunogenic composition of claim 15, wherein at least one secondary carrier is a protein or a peptide.

22. The dual carrier immunogenic composition of claim 21, wherein the protein or peptide is selected from the group consisting of viral, bacterial, parasitic, animal and fungal proteins or peptides.

23. The dual carrier immunogenic composition of claim 22, wherein the protein or peptide is selected from the group consisting of diphtheria toxoid, pertussis toxoid, tetanus toxoid, bacterial outer membrane protein, viral outer membrane protein, and combinations thereof.

24. The dual carrier immunogenic composition of claim 15, wherein at least one moiety is coupled to a primary carrier.

25. The dual carrier immunogenic composition of claim 15, wherein at least one moiety is chemically coupled to a secondary carrier.

26. The dual carrier immunogenic composition of claim 15, wherein at least one primary carrier is conjugated to a plurality of one or more secondary carriers.

27. The dual carrier immunogenic composition of claim 15, wherein at least one of the secondary carriers chemically conjugated to a primary carrier is further coupled to at least one hapten.

28. The dual carrier immunogenic composition of claim 15, further comprising an adjuvant.

29. A vaccine, comprising:
an immunostimulatory amount of at least one of the dual carrier immunogenic compositions of claim 15, and
a pharmaceutically acceptable carrier.

30. A method of treating a patient, comprising administering to the patient the vaccine of claim 29.

31. The method of claim 30, wherein the vaccine is administered intravenously, intramuscularly, or subcutaneously.

* * * * *

UNITED STATES PATENT AND TRADEMARK OFFICE
CERTIFICATE OF CORRECTION

PATENT NO. : 5,585,100
DATED : December 17, 1996
INVENTOR(S) : Mond et al.

It is certified that error appears in the above-indentified patent and that said Letters Patent is hereby corrected as shown below:

On title page, item [73] the Assignee should read as --Henry M. Jackson Foundation for the Advancement of Military Medicine--, instead of "Henry Jackson Foundation".

Signed and Sealed this

Third Day of November, 1998

Attest:

BRUCE LEHMAN

*Attesting Officer*  *Commissioner of Patents and Trademarks*